US008439937B2

(12) United States Patent
Montague et al.

(10) Patent No.: US 8,439,937 B2
(45) Date of Patent: May 14, 2013

(54) SYSTEM, APPARATUS AND METHOD FOR OPENING AN OCCLUDED LESION

(75) Inventors: James Robert Montague, Elk River, MN (US); Victor Roy Blackledge, Cologne, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 41 days.

(21) Appl. No.: 11/767,725

(22) Filed: Jun. 25, 2007

(65) Prior Publication Data

US 2008/0319462 A1 Dec. 25, 2008

(51) Int. Cl.
*A61B 17/22* (2006.01)

(52) U.S. Cl.
USPC ........................................................ 606/159

(58) Field of Classification Search .................. 606/159, 606/170–172, 180; 600/585; 604/22
See application file for complete search history.

(56) References Cited

U.S. PATENT DOCUMENTS

| | | | |
|---|---|---|---|
| 4,884,579 A * | 12/1989 | Engelson ...................... | 600/585 |
| 5,273,526 A | 12/1993 | Dance et al. | |
| 5,314,438 A | 5/1994 | Shturman | |
| 5,376,077 A * | 12/1994 | Gomringer .............. | 604/167.06 |
| 5,605,162 A | 2/1997 | Mirzaee et al. | |
| 6,017,319 A * | 1/2000 | Jacobsen et al. .............. | 600/585 |
| 6,059,767 A * | 5/2000 | Noriega ......................... | 604/523 |
| 6,328,750 B1 * | 12/2001 | Berry et al. ................... | 606/168 |
| 6,447,507 B1 | 9/2002 | Bednarek et al. | |
| 6,494,890 B1 * | 12/2002 | Shturman et al. ............. | 606/159 |
| 6,824,550 B1 | 11/2004 | Noriega et al. | |
| 2001/0021831 A1 | 9/2001 | Fleischhacker et al. | |
| 2003/0069522 A1 * | 4/2003 | Jacobsen et al. .............. | 600/585 |
| 2003/0125756 A1 * | 7/2003 | Shturman et al. ............. | 606/159 |
| 2005/0033334 A1 * | 2/2005 | Santra et al. .................... | 606/159 |
| 2005/0203553 A1 | 9/2005 | Maschke | |
| 2005/0283179 A1 | 12/2005 | Lentz | |
| 2006/0047222 A1 * | 3/2006 | Heuser ........................... | 600/585 |
| 2006/0074442 A1 * | 4/2006 | Noriega et al. ................ | 606/159 |
| 2008/0071303 A1 * | 3/2008 | Hacker et al. .................. | 606/180 |
| 2010/0010499 A1 * | 1/2010 | Fischer, Jr. .................... | 606/108 |

FOREIGN PATENT DOCUMENTS

| | | |
|---|---|---|
| EP | 0 480 427 | 4/1992 |
| JP | 2000254235 | 9/2000 |
| JP | 2005230550 | 9/2005 |
| WO | WO 97/43949 | 11/1997 |
| WO | WO 2004/012804 | 2/2004 |
| WO | WO 2004/060463 | 7/2004 |

* cited by examiner

*Primary Examiner* — Thomas McEvoy
(74) *Attorney, Agent, or Firm* — Winthrop & Weinstine, P.A.

(57) ABSTRACT

A system, apparatus and method for maximizing efficiency of tissue removal from body passageways is provided. The system comprises a device for opening an occluded lesion, e.g., a rotational atherectomy device or angioplasty device, and a guide wire having an introducer sheath. The guide wire introducer sheath may comprise a hypo tube having columnar strength greater than that of the guide wire alone to assist the guide wire in crossing occluded lesions, wherein the sheath and guide wire are axially moveable relative to each other. The guide wire sheath may further comprise increased flexibility at its distal end to increase flexibility and/or a soft distal tip to help with steerability through the vasculature. The sheath may allow for a smaller outer diameter guide wire which, in turn, may allow for a smaller outer diameter on the occlusion-opening device, e.g., atherectomy or angioplasty device, which is slid over the pre-positioned guide wire.

23 Claims, 4 Drawing Sheets

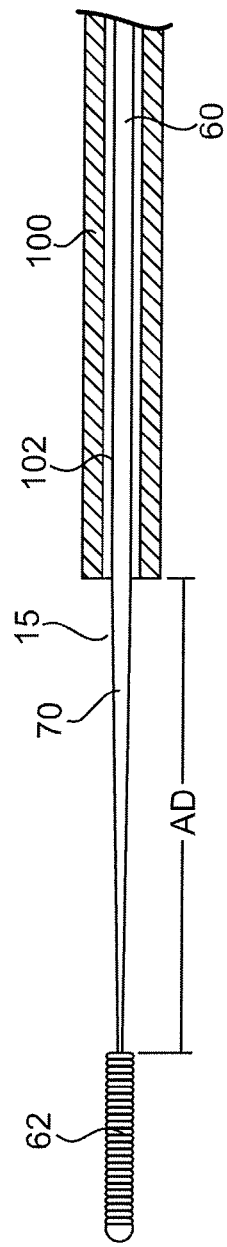
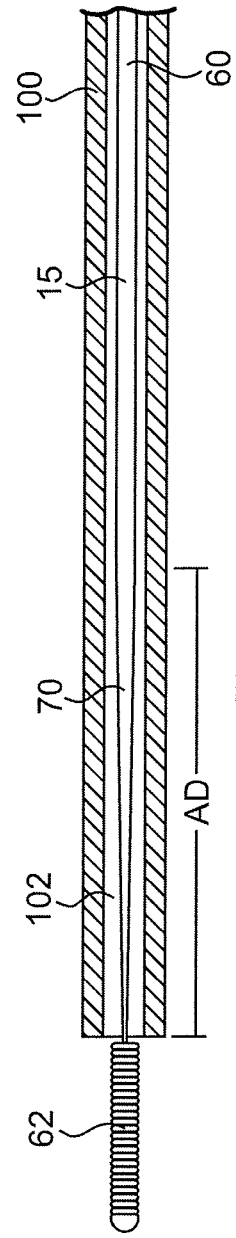

SYSTEM, APPARATUS AND METHOD FOR OPENING AN OCCLUDED LESION

BACKGROUND OF THE INVENTION

1. Field of the Invention

The invention generally relates to devices and methods for guide wires that are used generally in cardiovascular and endovascular procedures, more specifically in atherectomy and/or angioplasty procedures, to facilitate the placement of catheters for angioplasty procedures and/or rotating drive shafts for atherectomy procedures within the vasculature of patients.

2. Description of the Related Art

A variety of techniques and instruments have been developed for use in the removal and/or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a burr covered with an abrasive cutting material such as diamond particles is carried at the distal end of a flexible drive shaft. The burr is rotated at high speeds (typically, e.g., in the range of about 150,000-190,000 rpm) while it is advanced across the stenosis.

U.S. Pat. No. 5,314,438 (Shturman) discloses another atherectomy device having a drive shaft with a section of the drive shaft having an enlarged diameter, at least a segment of this enlarged cutting head being covered with an abrasive material to define an abrasive segment of the drive shaft. When rotated at high speeds, the abrasive segment is capable of removing stenotic tissue from an artery.

U.S. Pat. No. 6,494,890 (Shturman) discloses an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation.

Typically a steerable guide wire is prepositioned within the lumen of the artery to a position at a point typically beyond or distal the obstruction, thus the guide wire must cross the occluded lesion. The atherectomy drive shaft may then be slid forward or distally along and over the prepositioned guide wire until the drive shaft, more particularly the abrasive surface of the drive shaft, is positioned adjacent or otherwise proximal the obstruction. The guide wire is thus pre-positioned prior to advancement of the typically less flexible and less steerable atherectomy drive shaft to facilitate advancement and positioning of the drive shaft at or adjacent the obstruction.

As discussed above, the atherectomy may be followed by an angioplasty procedure, a therapeutic medical procedure in which a catheter or the like is inserted into a blood vessel to increase blood flow as a safer, less expensive alternative to by-pass surgery. Typically, as with the atherectomy drive shaft discussed above, a steerable guide wire passes through the catheter and is able to move independently of the catheter. The guide wire is moved into position at a point typically beyond or distal the obstruction. The catheter is then slid forward or distally along and over the guide wire until the catheter is positioned adjacent or otherwise proximal the obstruction. The guide wire is thus pre-positioned prior to advancement of the catheter to facilitate advancement and positioning of the catheter at or adjacent the obstruction.

Several forms of guide wires for use in atherectomy drive shaft device and/or catheter placement are known. The simplest form of guide wire comprises a preferred diameter of between about 0.20-1.0 mm. The distal end of the known guide wire may comprise a bent tip that may be oriented to guide the wire along a vascular path. These types of guide wires may be difficult to steer through a tortuous vasculature and may encounter frictional difficulties along the lumen.

Other known guide wires comprise a flexible sheath or coating fused or heat shrunk to the guide wire to facilitate movement through the lumen. Coated guide wires do not allow the guide wire to comprise a longer taper section on the tip while still retaining the necessary columnar strength and flexibility required to move through the vasculature and ultimately through the obstruction. These guide wires may also be undesirable in that the sheath or coating cannot be removed once the guide wire is in position. The fused or coated sheath also increases the diameter of the guide wire which, in turn, requires a larger inner diameter and associated outer diameter for the device sliding over the guide wire.

Guide wires used to facilitate placement of devices to open occluded lesions must balance flexibility, steerability and outer diameter parameters with columnar strength. Insufficient columnar strength results in guide wires that have a tendency to buckle under axial compression during the insertion procedure, most typically while crossing the occlusion.

It is desirable to keep the diameter of the system itself, including the guide wire, as small as possible while retaining the required functionality. The guide wire must have sufficient flexibility while retaining steerability and columnar strength to allow crossing of occluded lesions. The present invention addresses these needs.

BRIEF SUMMARY OF THE INVENTION

A system, apparatus and method for maximizing efficiency of tissue removal from body passageways is provided. The system comprises a device for opening an occluded lesion, e.g., a rotational atherectomy device or a catheter, and a guide wire having an introducer sheath. The guide wire introducer sheath may comprise a hypo tube having columnar strength greater than that of the guide wire alone to assist the guide wire in crossing occluded lesions, wherein the sheath and guide wire are axially moveable relative to each other. The guide wire introducer sheath may further comprise increased flexibility at its distal end to increase flexibility and/or a soft distal tip to help with steerability through the vasculature. The introducer sheath may allow for a smaller outer diameter guide wire which, in turn, may allow for a smaller outer diameter on the occlusion-opening device, e.g., atherectomy or angioplasty device, which is slid over the pre-positioned guide wire.

Advantageously, certain embodiments of the present invention provide a system, apparatus and method for improving the efficiency of tissue removal from body passageways, e.g., stenosis from arteries.

Another object of the invention is to provide a system, apparatus and method for improving the efficiency of rotational atherectomy procedures.

Another object of the invention is to provide a system, apparatus and method for improving the efficiency of angioplasty procedures.

Another object of the invention is to provide a system, apparatus and method for reducing trauma during positioning of a guide wire.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

FIG. 4A is a partial cutaway view of one embodiment of a guide wire extending outwardly from the guide wire introducer sheath.

FIG. 4B is a partial cutaway view of one embodiment of a guide wire with its tip extending outwardly from the guide wire introducer sheath.

DETAILED DESCRIPTION OF THE INVENTION, INCLUDING THE BEST MODE

Figure 1:
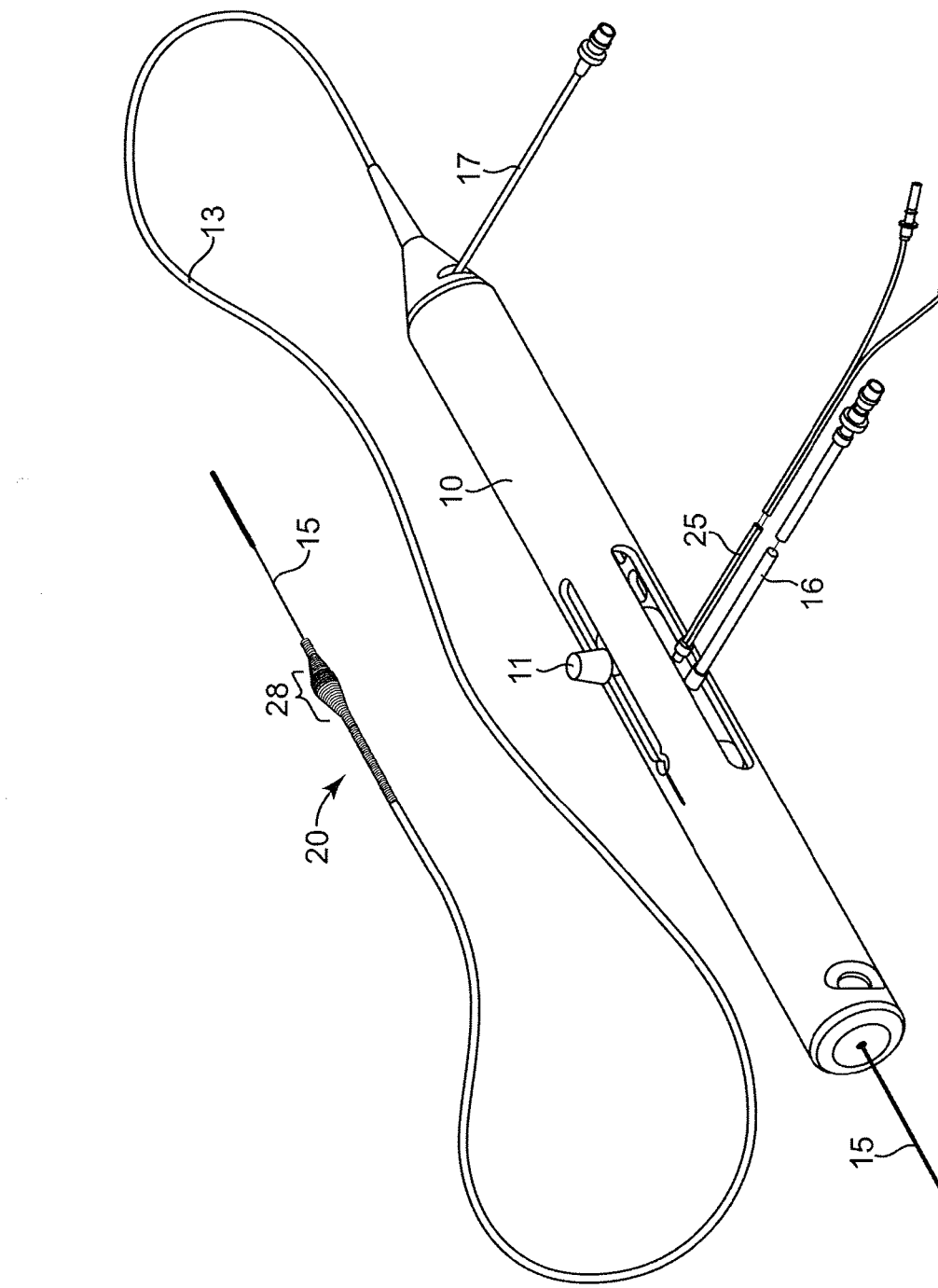
FIG. 1 is a perspective view of a prior art rotational atherectomy system.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 illustrates a typical and exemplary rotational atherectomy device that may utilize the present invention. Such a device is generally described in U.S. Pat. No. 5,314,438 (Shturman) and U.S. Pat. No. 6,494,890 (Shturman), the disclosures of each incorporated herein by reference in their entirety.

The exemplary rotational atherectomy device of FIG. 1 includes a handle portion 10, an elongated, flexible drive shaft 20, an enlarged cutting section 28, and an elongated catheter 13 extending distally from the handle portion 10. Enlarged cutting section 28 is shown as a solid piece attached to the drive shaft 20 for exemplary purposes. This form of cutting section 28 and others will be discussed further herein. The drive shaft 20 and enlarged cutting section 28 are constructed from helically coiled wire. The catheter 13 has a distal end and a lumen in which most of the length of the drive shaft 20 is disposed, except for its enlarged cutting section 28 and a short section distal to the enlarged cutting section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. The handle 10 also desirably includes a control knob 11 for advancing and retracting the turbine and drive shaft 20 with respect to the catheter 13 and the body of the handle.

With continued reference to FIG. 1, the catheter 13 has a lumen (not shown) in which most of the length of the drive shaft 20 may be typically disposed, except for its enlarged cutting section 28 and a short section distal to the enlarged cutting section 28. The drive shaft 20 also contains an inner lumen (not shown), permitting the drive shaft 20 to be advanced and rotated over a guide wire 15.

Thus, the device for opening an occlusion exemplified in FIG. 1 comprises an atherectomy device with an abrasive drive shaft that is slid and rotated over a pre-positioned guide wire. A similar pre-positioning technique is used with another device for opening an occlusion, the "over-the-wire" balloon catheter. This conventional device typically pre-positions a steerable guide wire within the bodily lumen, the angioplasty catheter is then advanced along the guide wire to position its balloon end portion across the lesion prior to inflation of the balloon and dilatation or opening of the stenosis or lesion. As discussed herein, systems, devices and methods for opening an occluded lesion or occlusion or stenosis are defined to comprise "over-the-wire" atherectomy and angioplasty systems, devices and methods.

Figure 2:
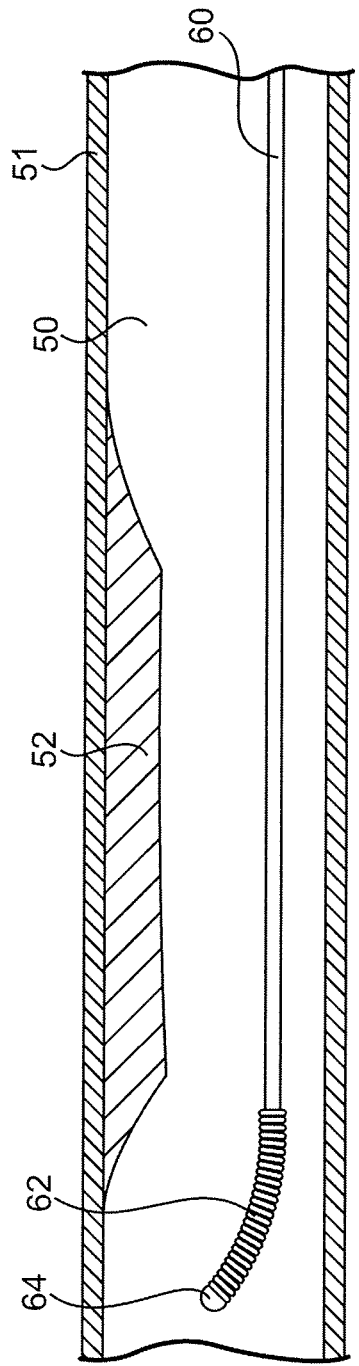
FIG. 2 is a partial cutaway view of one embodiment of a prior art guide wire within a bodily lumen that is partially occluded.
Figure 3:
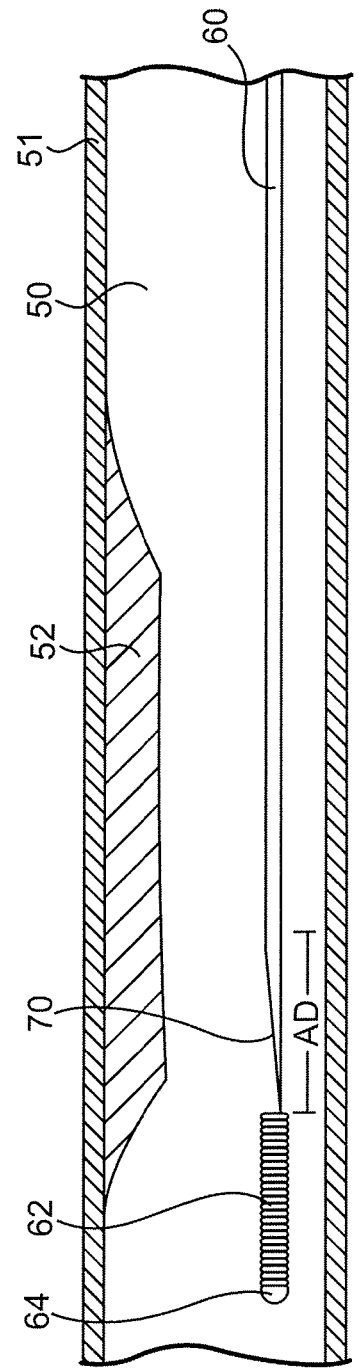
FIG. 3 is a partial cutaway view of one embodiment of a prior art guide wire within a bodily lumen that is partially occluded.

FIGS. 2 and 3 illustrate known embodiments of guide wire 15 in more detail and positioned within a bodily lumen 50, defined by e.g., an artery, adjacent to a partial occlusion 52. Guide wire 15 typically comprises an elongated shaft 60 and a conventional helically wound distal tip 62 terminating in a rounded tip 64. Conventional guide wires may further comprise some radiopaque material at or near the rounded tip 64 to facilitate positional monitoring and tracking of the device within the lumen 50 and in relation to the occlusion 52. FIG. 2 illustrates the helically wound distal tip 62 as being capable of bending away from the elongated shaft 60.

As shown in FIG. 3, some guide wires 15 may comprise a straight helically wound distal tip 62 and/or a tapered section 70 fixedly attached and proximally adjacent to the helically wound distal tip 62. The tapered section 70 comprises an axial length AD and an outer diameter that is smaller than the elongated shaft 60. Such a configuration may assist the operator in moving the guide wire 15 across an occluded lesion. However, as discussed above, a risk for such a configuration involves buckling of the guide wire 15 at the tapered section 70 at a point either proximal to the occlusion or within the occlusion itself. Such an eventuality is of course highly undesirable. As a result, the tapered section 70 may have a very short axial distance AD to minimize the possibility that the tapered section 70 may buckle under the axial pressure necessary to cross the occluded lesion. However, the shortened tapered section 70 may be too short to allow complete navigation across the occlusion. Moreover, a tapered section 70 of any axial length AD decreases the columnar strength of the guide wire at its tapered section 70, thus allowing for risk of buckling under axial pressure as the operator applies axial force in an effort to advance guide wire 15 through a lesion.

Turning now to FIGS. 4A and 4B, one embodiment of the inventive guide wire sheath 100 is illustrated. Sheath 100, as illustrated, comprises a lumen 102 therethrough, wherein the lumen 102 is capable of slidingly receiving guide wire 15. Sheath 100 closely surrounds guide wire 15, providing enhanced columnar strength to the guide wire 15 as the guide wire 15 and sheath 100 are advanced axially distally through a bodily lumen (not shown) along the way to and through an occluded lesion (not shown). The guide wire 15 and sheath 100 are, as illustrated, arranged to allow the guide wire 15 and sheath 100 independent axial movement relative to one another.

FIG. 4A illustrates the helically wound tip 62, tapered section 70, having an elongated axial distance AD as compared with prior art guide wire 15 as illustrated by FIGS. 2 and 3. A portion of the elongated shaft 60 is shown extending distally beyond the sheath 100. Such a configuration may result, e.g., after the guide wire 15 and sheath 100 have been moved distally through and beyond the occlusion and the sheath 100 pulled back proximally to expose the guide wire 15. Alternatively, the sheath 100 may be left in place following crossing of the occlusion.

FIG. 4B illustrates another possible configuration of the sheath 100 and the guide wire 15. As shown, the helically wound tip 62 extends beyond the sheath 100. Together, FIGS. 4A and 4B illustrate the independently axial movement of sheath 100 relative to guide wire 15.

Thus, the device for opening occlusions, e.g., a rotational atherectomy device or angioplasty device, may be slid over the pre-positioned guide wire 15 and sheath 100, or the sheath 100 may be slid back proximally so that the device for opening occlusions may be slid over the pre-positioned guide wire 15 at least partially without the sheath 100.

To achieve axial movement of the sheath 100 and/or guide wire 15 relative to each other, the sheath 15 may either be retracted, i.e., pulled back proximally, or advanced distally, while holding guide wire 15 in a relatively constant axial position. Alternatively, guide wire 15 may either be advanced distally or retracted proximally while holding sheath 100 in a relatively constant axial position. More alternatively, the sheath 100 and the guide wire 15 may be moved in opposing axial directions to accomplish the desired result.

As discussed briefly above, one advantage of the sheath 100 used in combination with the guide wire 15 is that the sheath 100 provides additional columnar strength. This, in turn, may allow for a smaller diameter guide wire 15 than prior art guide wires. For example, currently known guide wires may comprise an outer diameter of 0.20-1.0 mm. However, using the sheath 100 of the present invention, the guide wire 15 may comprise an outer diameter (O.D.) as small as 0.1 mm, thus the guide wire O.D. may be within the range of 0.1 mm to 1.0 mm; more preferably within the range of 0.1 mm to 0.5 mm; and still more preferably within the range of 0.1 mm to 0.1 mm.

The sheath 100 may comprise an O.D. of about 0.355 mm, when the guide wire comprises an O.D. of 0.1 mm. Thus, the sheath 100 may comprise an O.D. within the range of 0.3 mm to 1.4 mm; more preferably within the range of 0.3 mm to 0.9 mm; and still more preferably within the range of 0.3 mm to 0.5 mm.

This smaller guide wire 15 O.D. is made possible due to the additional support of the accompanying sheath 100 which provides enough columnar strength to enable the smaller O.D. guide wire 15 to move through the sometimes tortuous vasculature and/or through an occluded lesion without buckling under axial pressure and compression.

The smaller O.D. of guide wire 15 may, in turn, allow for a smaller shaft to be used by the device used to removed occluded lesions. For example, if the sheath 100 is removed after pre-positioning the guide wire 15, the rotational atherectomy drive shaft 20 may, in turn, have a smaller inner diameter as well as a smaller outer diameter while still being able to slide distally and proximally over the guide wire 15. This is desirable to reduce trauma and may allow access to blood vessels that otherwise may not be accessed by larger devices.

The protective and columnar strengthening qualities of the sheath 100 may allow the guide wire 15 to have a longer tapered section 70 than otherwise would be possible or feasible. A longer tapered section 70 may provide for improved atraumatic characteristics and may facilitate traversing particularly tortuous passageways and/or difficult lesions. This concept may be appreciated by comparing prior art guide wires 15 in FIGS. 2 and 3 having a much short tapered section 70 axial diameter AD than the guide wire 15 illustrated in connection with FIGS. 4A and 4B.

As used throughout herein, the terms "tapering," "taper," "tapered," "tapers," and variations thereof describe embodiments of the invention, rather than to provide any lexicographic definitions.

Figure 5A:
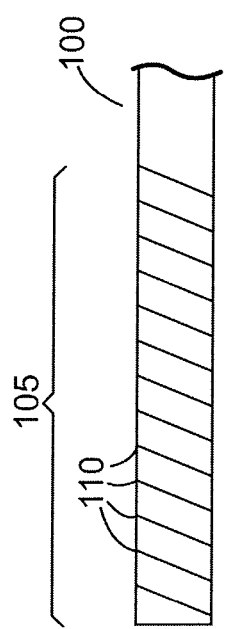
FIG. 5A is a top view illustrating one embodiment of a guide wire introducer sheath.
Figure 5B:
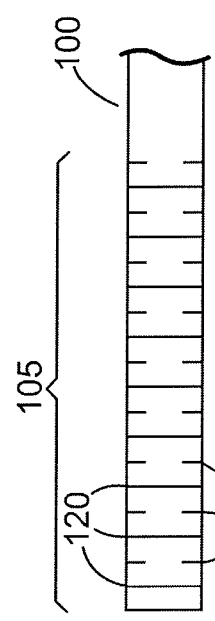
FIG. 5B is a top view illustrating one embodiment of a guide wire introducer sheath.

Turning now to FIGS. 5A and 5B, sheath 100 may comprise at least one striation section 105 wherein striations, cuts and/or slots may be provided at least partially through the sheath 100 surface. Exemplary striations are provided in the Figures. FIG. 5A provides an example of a continuous spiral cut striation 110 while FIG. 5B illustrates continuous circular cuts or striations 120 separated by discontinuous slotted cuts or striations 130. Such striations may be used to increase the flexibility of sheath 100 while retaining the desired level of columnar strength necessary to axially move the sheath 100 and guide wire 15 through the vasculature and across occluded lesions. The exemplary striations are illustrative only. Those skilled in the art will recognize equivalent forms of striations, each of which is within the scope and spirit of the present invention.

It is contemplated that preferably the distal end of the sheath 100 comprises such striations to facilitate and improve flexibility within the tortuous vasculature. However, those skilled in the art will recognize potential utility in either placing individual discrete striation sections 105 along at least a part of the length of the sheath 100 or, alternatively, substantially all of the sheath 100 length may comprise striations. Each such configuration is within the scope of the present invention.

Figure 6:
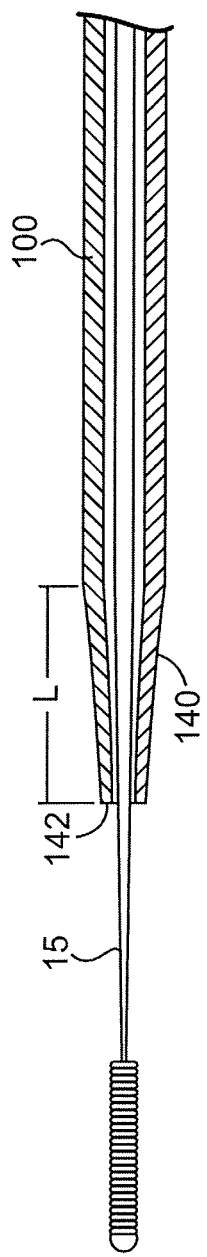
FIG. 6 is a partial cutaway view illustrating a guide wire introducer sheath with a tapered end and a guide wire with an elongated tapered section extending partially outwardly therefrom.

Sheath 100 may be cylindrical throughout its length, comprising substantially a constant diameter throughout. However, with reference now to FIG. 6, an alternate embodiment of the sheath 100 may comprise a soft, resilient and flexible atraumatic tip 140, having an axial length L and that may comprise soft plastic or soft rubber to facilitate steering the sheath 100 and accompanying guide wire 15 through vasculature with improved atraumatic results. The atraumatic tip 140 is shown comprising a taper which, in addition to facilitating steering the sheath 100 and guide wire 15 through vasculature, may further facilitate movement of the sheath 100 and guide wire 15 through an occluded lesion with less trauma than a sheath 100 without tip 140. Alternatively, the atraumatic tip 140 may not require a taper, instead utilizing soft plastic and/or thinner walls to create the desired resilience and flexibility. Atraumatic tip 140 may be resilient enough to easily bend around turns and contortions of the vasculature, essentially leading the sheath 100 and guide wire 15 through the vasculature without damaging the side walls of the lumen in the process.

Sheath 100 may be comprised of a less soft and/or less resilient material than atraumatic tip 140. Alternatively, sheath 100 may comprise the same material as atraumatic tip 140, wherein the softness and resilience between sheath 100 and tip 140 are substantially equivalent. Still more alternatively, the thickness of the walls of sheath 100 and tip 140 may be substantially equivalent or tip 140 may comprise walls that are thinner than the walls of the sheath 100. Such a configuration may provide additional flexibility to the tip 140.

The atraumatic tip 140 may taper over a partial length (or in another embodiment over the entire length) in a variety of ways. The taper may be created by progressively removing more material from the outer walls of the distal end of the sheath 100, wherein the atraumatic tip 140 comprises walls of decreasing thickness in the distal direction. Alternatively, the distance or gap between guide wire 14 and the inner diameter of sheath 100 may be decreased progressively along the distal end of sheath 100. Still more alternatively, a combination of the two embodiments to create the taper just discussed may be employed.

By way of example only and not by way of limitation, the atraumatic tip 140 when compared with the relatively constant diameter of sheath 100 to which tip 140 is operatively coupled may have a decreased, reduced, lesser, and/or smaller (individually and collectively, hereafter "smaller") cross sectional area, mean diameter, perimeter, volume over a given length, thickness in height and width, and/or other smaller configuration, shape, form, profile, structure, external outline, and/or contour (individually and collectively, "cross sectional area") during manufacturing, processing, molding, casting, forming, extruding, drawing and/or any combination thereof or equivalents thereto.

Tip 140 may taper all the way to the distal end 142 of tip 140 at a substantially constant angle. Alternatively, the tapering angle may vary and/or may cease tapering before reaching the distal end 142, leaving a distal-most nose portion of the tip 140 in the shape of a cylinder or the equivalent, i.e., a relatively constant diameter.

Atraumatic tip 140 is operably coupled with sheath 100 by methods well known to those skilled in the art.

By way of example only and not by way of limitation, the terms "operatively coupling," "operatively coupled," "coupling," "coupled," and variants thereof as used herein describe embodiments of the invention having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinched, press fit tight, nested, wedged, and/or otherwise associated by a joint, a junction, a juncture, a seam, a union, a socket, a melt bond, glue, adhesives, resins, welding (laser, spot, etc.), soldering, brazing, adhesives, chemical bonding materials, implanted arrangement, or combinations thereof.

The sheath 100 and/or atraumatic tip 140 may be manufactured of plastic material, preferably a polymer, such as TEFLON TM, polyolefin or polyurethane, having a low-friction surface or which is amenable to coating with a low-friction material. Other suitable materials may include a sheath 100 formed of lubricious PTFE, polyester, polycarbonate, polyvinylchloride, latex, silicon rubber, polystyrene and polyacrylic. Surface coatings, if used, may comprise materials that comprise low-friction and/or which may be highly hydrophilic. Such coatings may be formed of polyvinylpyrrolidone (PVP), polyethyleneoxide or polyhydroxyethylmethacrylate (polyHEMA) or copolymers thereof. Further, the sheath 100 material and/or coating may be formed of lubricious materials. The sheath 100 may further be comprised of stainless steel.

Atraumatic tip 140 may comprise a striated section 105 as discussed above. Alternatively, at least one striated section 105 may cover the non-tapered section of sheath, in combination with atraumatic tip 140 which may, or in an alternate embodiment may not, comprise a striated section 105.

A method according to the present invention for maximizing efficiency of tissue removal from body passageways may comprise: providing a device for opening occluded lesions; providing a guide wire with introducer sheath; pre-positioning guide wire with introducer sheath; axially moving guide wire and introducer sheath to expose guide wire's helically wound tip; advancing the device for opening occluded lesions distally along the guide wire and sheath to the desired location; opening the occluded lesion.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:
1. A system for opening occlusions, comprising:
   a device for opening occlusions, the device comprising:
      a catheter comprising a lumen therethrough;
      a drive shaft received within the catheter lumen and comprising a helically coiled wire, an enlarged cutting section and a lumen therethrough, the drive shaft capable of high-speed rotation;
   a guide wire having a columnar strength, received within the drive shaft lumen and wherein the drive shaft is advanceable and rotatable over the guide wire, the guidewire comprising:
      an elongated shaft having a tapered distal section; and
      a helically wound distal tip fixedly attached and arranged distal to the tapered distal section;

a sheath having a columnar strength greater than the columnar strength of the guide wire and received within the drive shaft lumen and further having a distal end and a lumen that receives at least a portion of the guide wire, wherein the catheter, drive shaft, sheath and guide wire are axially and independently moveable relative to each other, wherein during use of the device, the sheath and guide wire are pushed through vasculature together toward an occlusion, the sheath providing columnar strength to the elongated shaft and tapered distal section of the guide wire thereby enabling the sheath and guide wire to push through the occlusion and wherein during further use of the device the drive shaft is next advanced over the sheath to the occlusion for removal of occlusive material; and an atraumatic tip operatively coupled to the distal end of sheath, wherein the atraumatic tip comprises a material that is more flexible than material comprising the sheath, and wherein the atraumatic tip has a tapered section wherein at least a portion of the walls of the atraumatic tip are thinner than the walls of the sheath.

2. The system of claim 1, wherein the sheath comprises at least one striation section.

3. The system of claim 2, wherein the at least one striation section comprises a continuous spiral cut striation.

4. The system of claim 2, wherein the distal end of the sheath comprises at least one striation section.

5. The system of claim 2, wherein the at least one striation section covers substantially the all of the sheath.

6. The system of claim 2, wherein the at least one striation section comprises a discontinuous slotted cut striation.

7. The system of claim 6, wherein the at least one striation section further comprises a continuous spiral cut striation.

8. The system of claim 1, wherein the atraumatic tip comprises at least one striation section.

9. The system of claim 1, wherein the sheath comprises a plastic material.

10. The system of claim 9, wherein the plastic material is lubricious.

11. The system of claim 9, wherein the plastic material is selected from the group consisting of Teflon, polyolefin, polyurethane, lubricious PTFI, polyester, polycarbonate, polyvinylchloride, latex, silicon rubber, polystyrene and polyacrylic.

12. The system of claim 9, wherein the sheath further comprises a surface coating disposed on the plastic material.

13. The system of claim 12, wherein the surface coating is hydrophilic.

14. The system of claim 13, wherein the surface coating is selected from the group consisting of polyvinylpyrrolidone, polyethyleneoxide, polyhyroxyethylmethacrylate and copolymers thereof.

15. The system of claim 1, wherein the sheath comprises stainless steel.

16. The system of claim 1, wherein the guide wire comprises an outer diameter within the range of 0.1 mm to 1.0 mm.

17. The system of claim 16, wherein the guide wire comprises an outer diameter within the range of 0.1 mm to 0.5 mm.

18. The system of claim 17, wherein the guide wire comprises an outer diameter within the range of 0.1 mm to 0.2 mm.

19. The system of claim 1, wherein the sheath comprises an outer diameter within the range of 0.3 mm to 1.4 mm.

20. The system of claim 19 wherein the sheath comprises an outer diameter within the range of 0.3 mm to 0.9 mm.

21. The system of claim 20 wherein the sheath comprises an outer diameter within the range of 0.3 mm to 0.5 mm.

22. The system of claim 1, wherein during use of the system, the sheath provides columnar support for the guide wire within a patient's vasculature.

23. The system of claim 1, wherein the device for opening occlusions comprises an atherectomy device.

\* \* \* \* \*